(12) United States Patent
Leiner et al.

(10) Patent No.: US 10,021,883 B2
(45) Date of Patent: Jul. 17, 2018

(54) HIGH SPEED RINSING SOLUTION APPLICATION

(71) Applicant: MPSC, Inc., Hudson, WI (US)

(72) Inventors: Andrew Michael Leiner, Burleigh Heads (AU); Earnest DeWayne Tooley, Hudson, WI (US); Ulises Pardo Arche, Culiacán (MX)

(73) Assignee: MPSC, Inc., Hudson, WI (US)

( * ) Notice: Subject to any disclaimer, the term of this patent is extended or adjusted under 35 U.S.C. 154(b) by 0 days.

(21) Appl. No.: 15/668,103

(22) Filed: Aug. 3, 2017

(65) Prior Publication Data

US 2018/0035680 A1 Feb. 8, 2018

Related U.S. Application Data

(60) Provisional application No. 62/370,460, filed on Aug. 3, 2016.

(51) Int. Cl.
*A22B 5/00* (2006.01)
*A61M 25/00* (2006.01)

(52) U.S. Cl.
CPC .............. *A22B 5/0082* (2013.01); *A22B 5/00* (2013.01); *A61L 2202/00* (2013.01); *A61M 25/00* (2013.01)

(58) Field of Classification Search
CPC .......... A22C 17/16; A22B 5/00; A22B 5/0082
USPC ....................................... 452/123, 173, 177
See application file for complete search history.

(56) References Cited

U.S. PATENT DOCUMENTS

| 5,007,336 | A |   | 4/1991 | Bernhardt et al. |
| 5,882,253 | A | * | 3/1999 | Mostoller ............ A22C 21/0061 |
|           |   |   |        | 452/173 |
| 5,931,730 | A |   | 8/1999 | Bernhardt et al. |
| 5,938,519 | A | * | 8/1999 | Wright .................... A22C 21/04 |
|           |   |   |        | 452/173 |

(Continued)

FOREIGN PATENT DOCUMENTS

| EP | 2086336 B1 | 8/2009 |
| WO | 2006010194 A1 | 2/2006 |

OTHER PUBLICATIONS

International Search Report and Written Opinion from related PCT Application No. PCT/US2017/045311, dated Oct. 10, 2017, 13 pages.

*Primary Examiner* — Richard T Price, Jr.
(74) *Attorney, Agent, or Firm* — Brooks, Cameron & Huebsch, PLLC

(57) ABSTRACT

The present disclosure includes various method, and apparatus embodiments for high speed rinsing solution application. One such apparatus embodiment includes a substructure having an elliptical track, a catheter delivery system including a plurality of carriages coupled to the track, wherein each of the carriages includes a respective catheter delivery mechanism, a carousel drive system configured to drive the carriages such that the carriages circulate about the substructure on the track, a rotary timing valve positioned above a central portion of the substructure, the rotary timing valve including a plurality of outlets each positioned at a respective radial position on the rotary timing valve, wherein each of the plurality of outlets is connected to a respective catheter delivery mechanism by a hose, and a hose table positioned between the rotary timing valve and the substructure and configured to support the hoses.

20 Claims, 5 Drawing Sheets

(56) References Cited

U.S. PATENT DOCUMENTS

| | | | | |
|---|---|---|---|---|
| 6,468,145 B1 * | 10/2002 | Houtz | ................... | A22C 17/16 |
| | | | | 452/123 |
| 7,828,636 B2 * | 11/2010 | Larson | ................... | A22C 17/16 |
| | | | | 452/123 |
| 8,012,002 B2 * | 9/2011 | Brown | ................ | A22B 5/0082 |
| | | | | 452/173 |
| 8,246,429 B2 * | 8/2012 | Hilgren | .............. | A22C 21/0061 |
| | | | | 452/123 |
| 8,684,799 B2 * | 4/2014 | Brink | ................ | A22C 21/0061 |
| | | | | 452/173 |

* cited by examiner

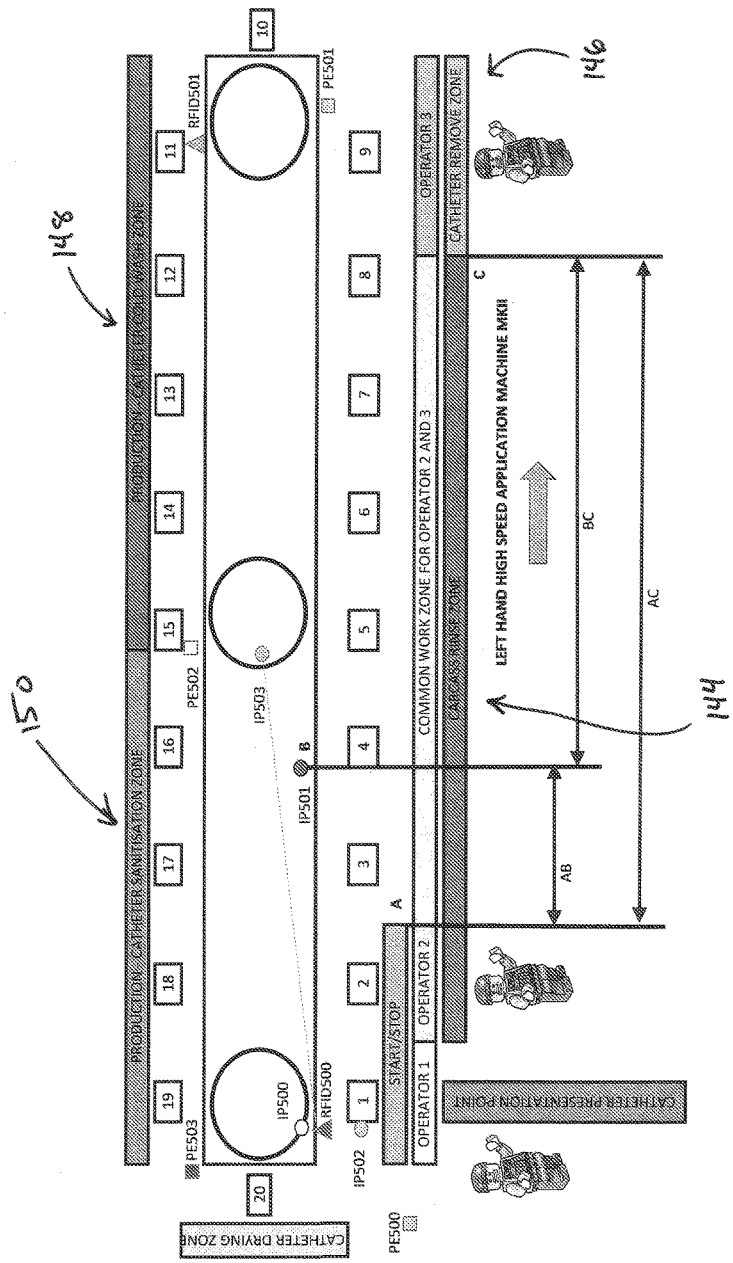

HIGH SPEED RINSING SOLUTION APPLICATION

PRIORITY INFORMATION

This application claims the benefit of U.S. Provisional Application Ser. No. 62/370,460, filed Aug. 3, 2016, the entire specification of which is incorporated herein by reference.

BACKGROUND

Treatment of slaughtered animals by injecting a treatment solution into the circulation system of the slaughtered animals provides for improved meat quality and improved yield. Such processing, also called "rinsing," involves the removal of the blood from the animal and the introduction of the treatment solution into the circulatory system. An example apparatus for administering a treatment solution to animals such as cattle, horses, hogs, poultry, deer, buffalo, sheep among others is described in U.S. Pat. No. 5,007,336, and is incorporated herein by reference. An example slaughtering process is described in U.S. Pat. No. 5,964,656, and is incorporated herein by reference.

BRIEF DESCRIPTION OF THE DRAWINGS

FIG. 5 is a top view diagram of the apparatus and associated zones in accordance with one or more embodiments of the present disclosure.

DETAILED DESCRIPTION

Figure 1:
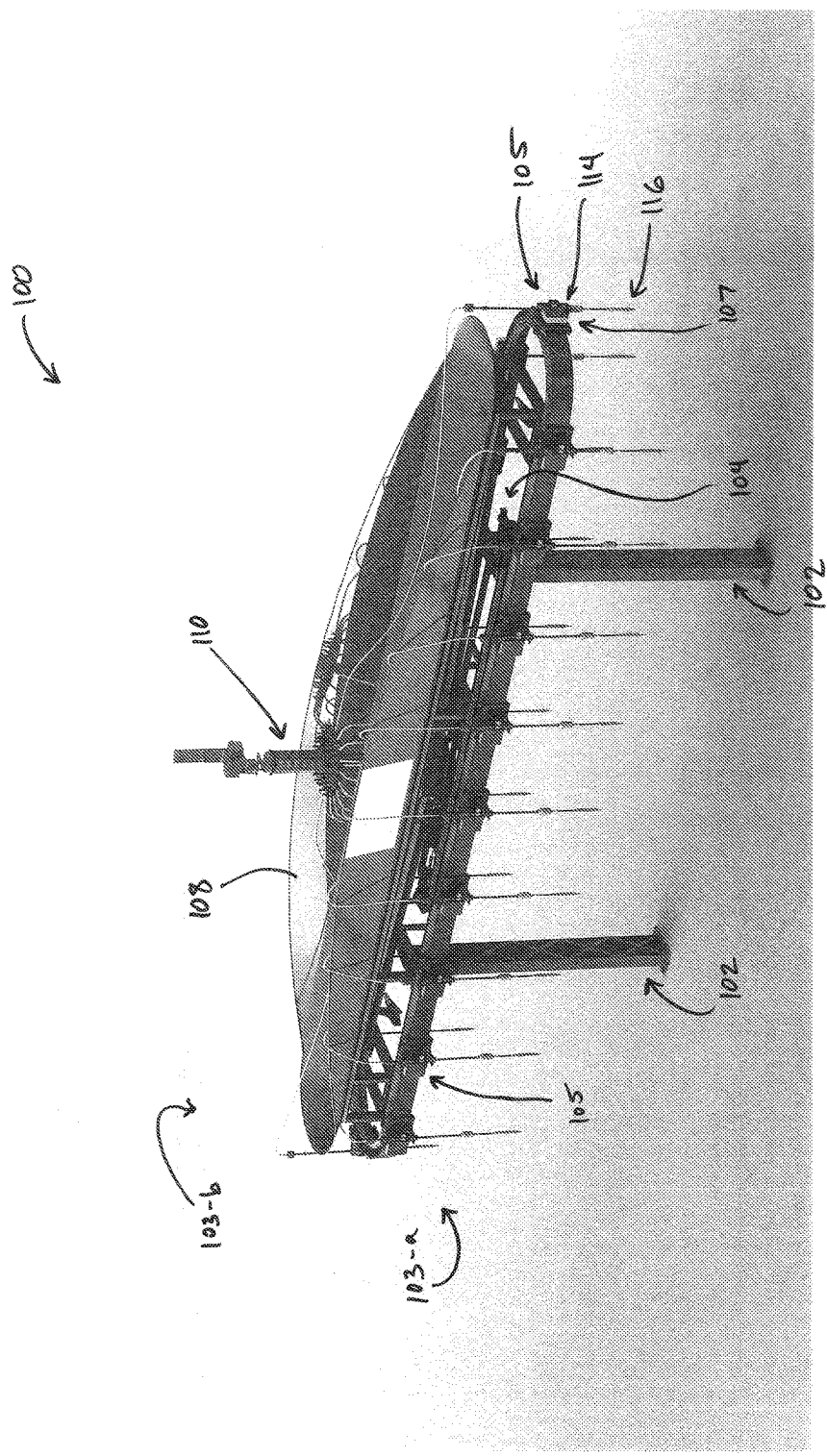
FIG. 1 illustrates an apparatus for high speed rinsing solution application in accordance with one or more embodiments of the present disclosure.

Treatment of slaughtered animals is complicated by a number of factors. Meat processing centers often have the capacity to process hundreds or even thousands of animals each day. Therefore, high speed processing can be beneficial in order to satisfy the capacity of these large meat processing centers. It is therefore desirable to streamline administration of the injection solution during meat processing.

Administration of the treatment solution also should be performed under exacting conditions. For instance, delivery of a treatment solution should occur at a consistent pressure that is high enough to ensure distribution through the entire animal while not rupturing the blood vessels. The treatment process can also be complicated by the desirability of maintaining sanitation of the devices put into contact with the animals and/or retaining the injection nozzle in the animal's circulatory system during treatment.

Various method, apparatus, and system embodiments for high speed rinsing solution application are described herein. In some embodiments, a high speed application apparatus is provided for the safe and hygienic delivery of a rinsing solution to the circulatory system (e.g., heart) or other suitable location of an animal (e.g., a sheep, pig, cow, etc.).

As an example, the animal can be positioned in a supine position and the solution delivered into the left ventricle of the animal. In some embodiments, 6.5 liters of solution can be delivered in a time period of 30 seconds. Embodiments of the present disclosure can allow the delivery of the solution at a rate that matches a rate of an existing slaughter line. For example, whereas fewer than eight animals per minute can be treated manually, embodiments of the present disclosure can allow solution to be delivered to greater than eight animals per minute (e.g., 13 per minute).

Embodiments of the present disclosure can include an apparatus having a plurality of carriages driven by a common drive train and circulating around an oval-shaped carousel track. "Oval-shaped" as referred to herein can include ellipsoidal shapes, stadium shapes, and others. The track can be defined by two major and substantially linear sides: an operator side and a sanitizing side (sometimes referred to herein as "non-operator side"). For instance, on the operator side, one or more operators can interact with the apparatus. Conversely, operators may be discouraged from entering the sanitizing side.

Each of the carriages can include a catheter delivery mechanism (CDM) extending therefrom in a downward direction. Rinsing solution can be metered into the catheter of each CDM on the operator side of the apparatus. An operator can initiate a rinse sequence following manual placement of a catheter into the circulatory system (e.g., heart) of a recently-slaughtered animal. The carriages can travel around the track at a same rate as a main animal conveyer and follow the animals along the track while delivering the solution along the operator side of the apparatus.

At the exit end of the operator side of the apparatus, the catheter can be removed from the animal. The catheter can be retracted into a suitable position and proceed with the carriage around to the sanitizing side into an ambient temperature water wash zone for a particular period of time (e.g., 10 seconds). The catheter can then continue into a sanitizing zone on the sanitizing side where it can be sprayed with hot potable filtered water of a particular temperature for a particular period of time (e.g., at least 85 degrees Celsius for 10 seconds). Once sanitized, the catheter carried by its respective carriage can arrive back on the operator side where it can again be placed into the circulatory system of another animal and the process can be repeated.

In the following detailed description, reference is made to the accompanying drawings that form a part hereof. The drawings show by way of illustration how one or more embodiments of the disclosure may be practiced.

These embodiments are described in sufficient detail to enable those of ordinary skill in the art to practice one or more embodiments of this disclosure. It is to be understood that other embodiments may be utilized and that process, electrical, and/or structural changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense FIG. 1 illustrates an apparatus for high speed rinsing solution application according to one or more embodiments of the present disclosure. Generally, the apparatus 100 includes a substructure 102, a carousel drive system 104, a catheter delivery system 106, a hose table 108, and a rotary timing valve 110. The apparatus 100 can additionally include machine covers and/or cladding, which are not shown in FIG. 1 so as not to obscure embodiments of the present disclosure. Additionally, the apparatus 100 can include a wash and sterilization system (obscured in FIG. 1) which can include various sterilizers, baths, and/or dryers. The apparatus can include two sides: an operator side 103-a and a sanitizing side 103-b.

The substructure 102 can include a support frame upon which a vertically-oriented metal track can be mounted together with a cam roller rail. As shown in FIG. 1, the substructure 102 can include a pair of support legs, though embodiments of the present disclosure are not so limited. The substructure 102 can support the remaining components of the apparatus 100 at a suitable height above ground such that animals can be guided underneath the catheter delivery system 106 of the apparatus 100.

The carousel drive system 104 can supply forward motion to a plurality of carriages 105 which can circulate on the metal track supported by the substructure 102. In the example illustrated in FIG. 1, twenty carriages 105 are included in the apparatus 100, though embodiments herein are not limited to a particular number of carriages. A respective CDM can be mounted to each of the carriages 105 (discussed further below in connection with FIG. 2).

The carousel drive system 104 can include a driven chain which can run within a guide that has, at a particular interval (e.g., 940 millimeters), a drive pin arrangement which rests within a respective slot machined into a tag attached to each of the carriages 105. The carousel drive system 104 can include a synchronous servomotor which can be coupled to a suitable reduction gearbox. The drive system 104 can operate to move the carriages 105 at a rate (e.g., speed) substantially matching that of a conveyor carrying the animals.

The catheter delivery system 106 can include a respective CDM 114 on each of the carriages 105. The CDM 114 can permit the positioning of a catheter 116 into an appropriate position for animal rinsing, nozzle washing, and/or nozzle sanitization.

Though not shown in FIG. 1 for purposes of clarity, the rotary timing valve 110 can be connected to each of the CDMs 114 by a respective hose. Fluid can be supplied through the rotary timing valve 110 to each of the hoses and then to each of the CDMs 114 located on the operator side 103-a. The hoses and their path of travel around the apparatus 100 is described in more detail in connection with FIG. 3; the rotary timing valve 110 is described in further detail in connection with FIGS. 4 and 5.

Figure 2:
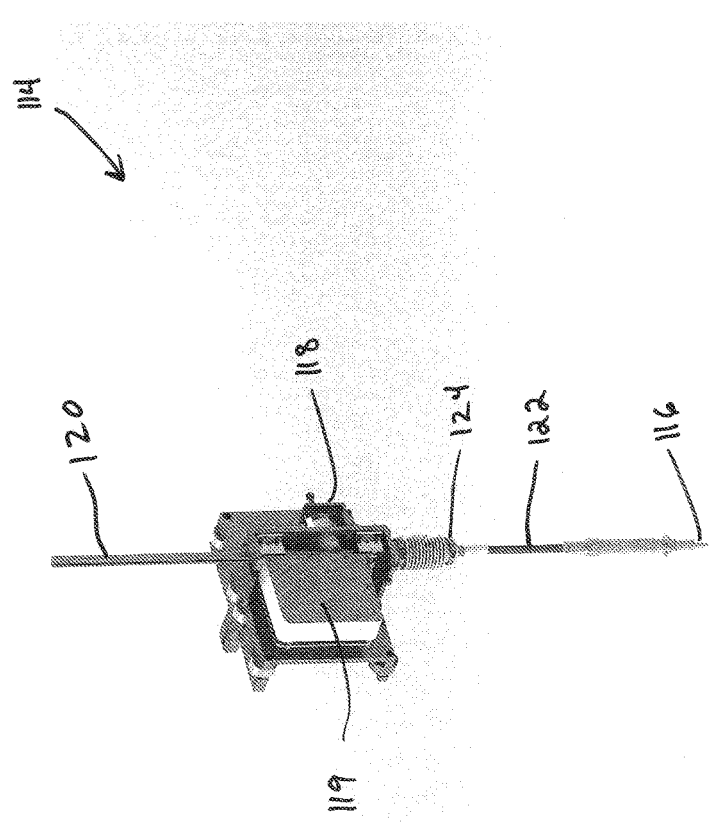
FIG. 2 illustrates a catheter delivery mechanism (CDM) in accordance with one or more embodiments of the present disclosure.

FIG. 2 illustrates a catheter delivery mechanism (CDM) 114 in accordance with one or more embodiments of the present disclosure. The CDM 114 can be one of a plurality of CDMs, each of which can be mounted to a respective carriage 105, for instance. In some embodiments, the apparatus 100 can include 20 such carriages 105, though embodiments of the present disclosure are not limited to a particular number.

As shown in FIG. 2, the CDM 114 can include a locking mechanism 118, a spring balance 119, a cam roller assembly 124, a shaft portion 120, a hose portion 122, and a catheter 116. In some embodiments, the locking mechanism 118 can include an inertial locking mechanism and/or a spring-loaded brake. The shaft portion 120 can be a hollow metal rod, for instance, such as a stainless steel rod. The hose portion 122 can be a length (e.g., 12 inches) of flexible tubing of a suitable thickness (e.g., 12 millimeters).

The cam roller assembly 124 can allow for vertical movement of the shaft portion 120 (and, thereby, the hose portion 122 and catheter 116) from a "home" position into an "operator" position (discussed below). The locking mechanism 118 can then selectively fix a vertical position of the shaft portion 120 in the "operator position" which can be overcome by an operator through downward force. In some embodiments, the shaft portion 120 can be held under tension by the spring balance 119 and adjusted up or down by an operator against resistance provided by the spring balance 119. In some embodiments, the shaft portion 120 can be pneumatically actuated to move from the home position to the operator position or vice versa. Stated differently, in some embodiments, an air cylinder can drive the shaft portion from the home position to the operator position.

In use, the CDM 114 can have three general positions. A first, "up" or "home" when not in use by an operator; a second, "operator position," in which it is capable of being manipulated by an operator; and a third, "in heart," when pinched between a cut rib cage and a rinse is underway. In the "home" position, the shaft portion 120 can be retracted to its highest point vertically. In the "in heart" position, the shaft portion 120 can be extended to its lowest point vertically. In the "operator position," the shaft portion 120 can be at a vertical position between those extremes (e.g., 5-6 inches below the "home" position).

An operator can extract the catheter 116 by manually drawing it down from an operator position. Once extracted, the catheter 116 can be inserted into the circulatory system of a animal and the operator can depress a "rinse start" button to initiate a rinse. The catheter can travel with the animal around a portion of the apparatus 100 during the rinse until it reaches the end of the operator side 103-a where it can be withdrawn from the animal upon termination of the rinse. When withdrawn, the catheter 114 can automatically return to its "home" position (e.g., when the cam roller assembly 124 inclines up).

If the catheter 116 is not withdrawn from the animal upon reaching the end of the operator side 103-a of the apparatus 100, the drive system 104 can stop. If the catheter 116 is in a retracted (e.g., nested) position, the carriage 105 carrying the CDM 114 can continue to a wash station located on the sanitizing side 103-b of the apparatus 100.

Figure 3:
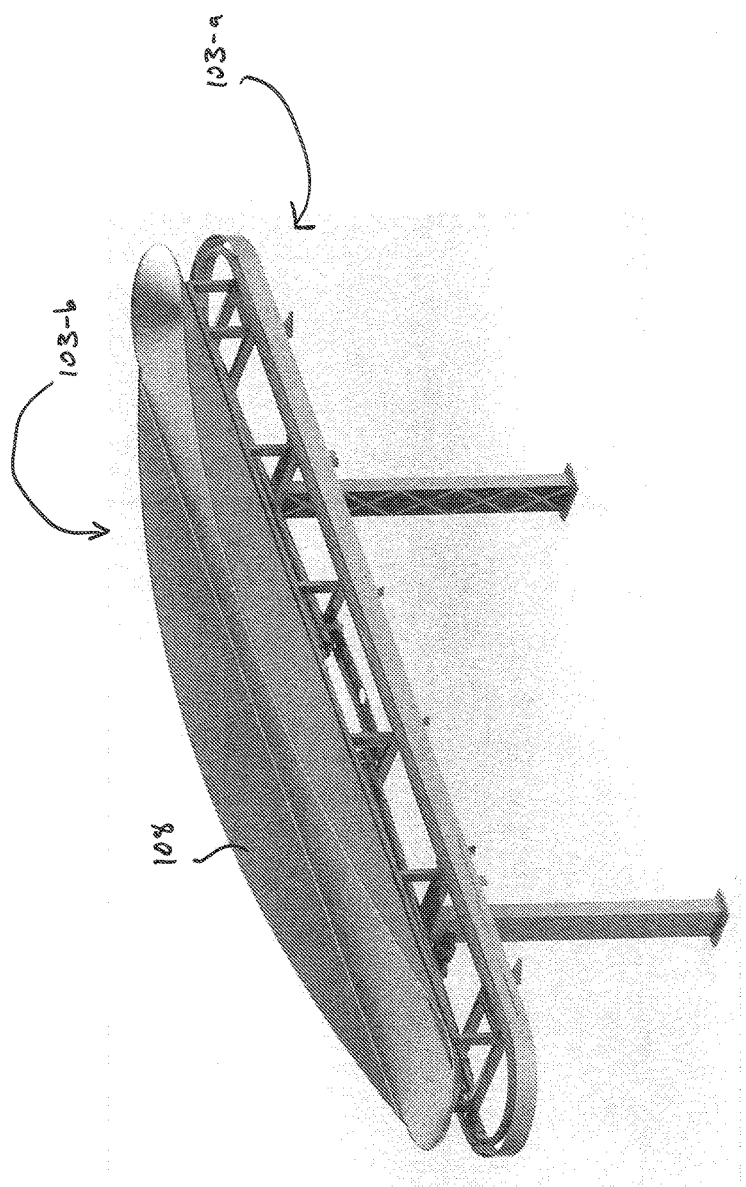
FIG. 3 illustrates a hose table in accordance with one or more embodiments of the present disclosure.

FIG. 3 illustrates a hose table 108 in accordance with one or more embodiments of the present disclosure. In various embodiments, the hose table 108 can be static such that the carriages 105 circulate around and below a perimeter of the hose table 108. On its major sides (e.g., the operator side 103-a and the non-operator (sanitizing) side 103-b), the hose table may be elevated. As shown, a raised lip or edge may pronounced along the operator side 103-a and the sanitizing side 103-b. As previously shown in FIG. 1, and as shown below in FIG. 4, the rotary timing valve 110 can extend through a central portion of a base of the hose table 108. A plurality of hoses can be connected at radial positions of the rotary timing valve 110 and can extend outwardly therefrom.

As described further below, each of the hoses can be connected to a respective one of the carriages 105. As the carriages 105 circulate around the hose table 108, the rotary timing valve 110 can rotate. A shape of the hose table 108 can be selected such that an amount of slack in a hose between the rotary timing valve 110 and a connected carriage remains substantially constant regardless of the position of the carriage in the circuit around the hose table 108. Thus, the hoses connecting the rotary timing valve 110 to the carriages 105 can trail the carriages 105 as they circulate without becoming entangled. The hose table 108 can provide support for each hose whether its carriage 105 is located at a distal end of the hose table 108 or on either side of the hose table 108.

Figure 4:
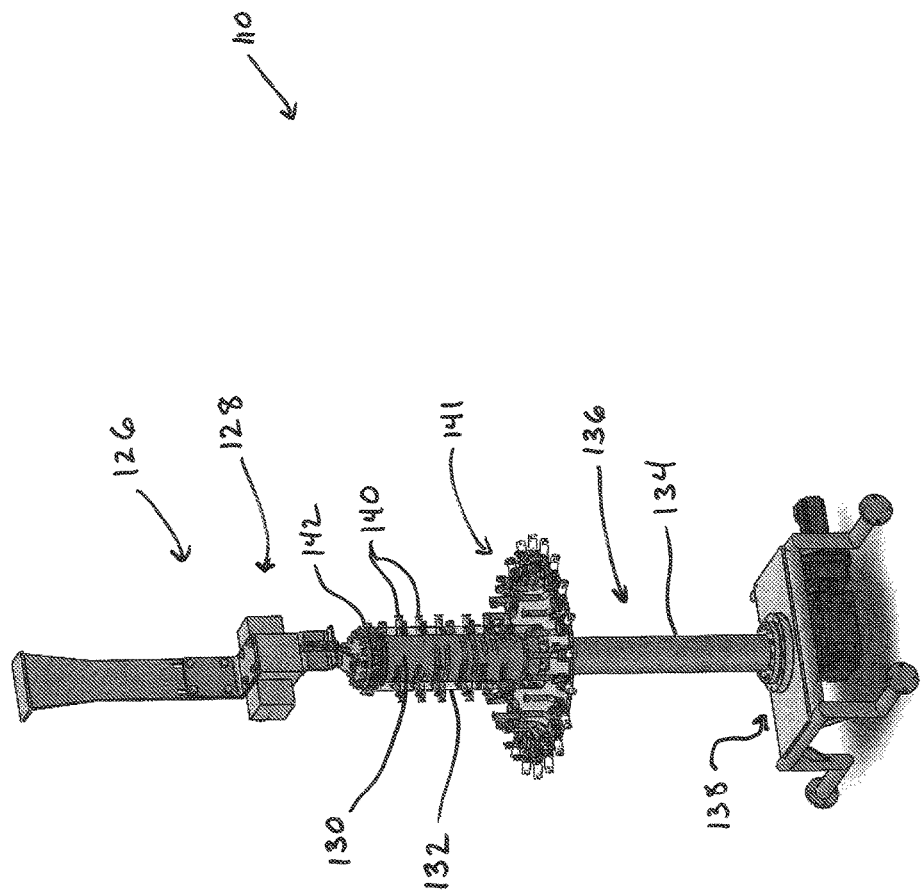
FIG. 4 illustrates a perspective view of a rotary timing valve in accordance with one or more embodiments of the present disclosure.

FIG. 4 illustrates a perspective view of a rotary timing valve 110 in accordance with one or more embodiments of the present disclosure. As shown in FIG. 4, the rotary timing valve 110 can include a roof and rotary actuator mounting bracket assembly 126, a rotary actuator and coupling assembly 128, a fixed valve portion 130, a rotating valve portion 132, a support column 134, a drive shaft 136, and a drive sprocket 138. As previously discussed, the rotary timing valve 110 (e.g., the drive shaft 136) can extend through the hose table 108.

The rotating valve portion 132 can include a plurality of (e.g., 20) outlet ports 140 for hose connection to CDMs 114, in some embodiments. Each of the outlet ports 140 can be connected to a respective carriage 105 (e.g., CDM 114 of the respective carriage 105) by a hose (not illustrated in FIG. 4 so as not to obscure embodiments of the present disclosure). As the carriages circulate about the apparatus 100, the rotating valve portion 132 can rotate freely allowing flow of rinsing solution to be provided to each CDM 114 on the operator side 103-a of the apparatus 100. In some embodiments, such as that shown in FIG. 4, each of the outlet ports can be connected via a respective hose to a peripheral outlet ring 141 at a base of the rotary timing valve 110. Rinsing solution can flow from the outlet ports 140, through the peripheral outlet ring 141, and then to each CDM 114.

The fixed valve portion 130 can be located internal to the rotating valve portion 132 and can include a number of inlet ports (e.g., 10 inlet ports) 142. The inlet ports 142 can receive rinsing solution from a source, such as a tank, reservoir, pump, etc.

The rinsing solution can flow into the rotary timing valve 110 through the inlet ports 142 and pass through openings of the fixed valve portion 130 such that half (e.g., approximately 180 degrees) of the fixed valve portion 130 includes the openings. Accordingly, liquid can flow into the fixed valve portion 130 through the inlet ports 142, out of one of the openings, and then out of one of the outlet ports of the rotary valve portion 132 as it aligns with one of the openings.

The fixed valve portion 130 can be rotated as desired such that liquid flow therethrough is directed in a particular direction. For instance, liquid can be directed towards the operator side 103-a of the apparatus 100, the non-operator side 103-b of the apparatus 100, and/or positions therebetween. When rinsing animals, flow can be permitted towards the operator side 103-a of the apparatus 100. When cleaning the apparatus 100, such as during the performance of a clean-in-place operation, flow can be permitted towards the non-operator side 103-b of the apparatus 100.

In order to rotate the fixed valve portion 130, the rotary actuator and coupling assembly 128 can be connected to the fixed valve portion 130 and cause rotation of the fixed valve portion 130 with respect to the roof and rotary actuator mounting bracket assembly 126 connected to a ceiling or a suitable fixed structure. The rotary timing valve 110 can be fixed at its base by a support column 134, which can be bolted to the hose table 108 and hermetically sealed to prevent microorganism growth and/or moisture intrusion, for instance. The rotary actuator and coupling assembly 128 can include an inlet/outlet port, for instance, which may be used for the passage of clean industrial air (e.g., at a maximum of 7 bar).

A drive shaft 136 can extend through the support column 134 and connect to a drive sprocket 138 below the hose table 108. As the rotary timing valve 110 is supported at its base via the support column 134, the top of the rotary timing valve 110 may be not fixed and can be allowed to move by flexible resilient bushes. A certain degree of movement may be desirable to minimize wear on the mating components of the rotary timing valve 110.

As previously discussed, the fixed valve portion 130 can be rotated as desired such that liquid flow therethrough is directed in a particular direction. For instance, liquid can be directed towards the operator side 103-a of the apparatus 100 or the non-operator side 103-b of the apparatus 100. When rinsing animals, flow can be permitted towards the operator side 103-a of the apparatus 100. When cleaning the apparatus 100, such as during the performance of a clean-in-place operation, flow can be permitted towards the non-operator, sanitizing side 103-b of the apparatus 100.

FIG. 5 is a top view diagram of the apparatus 100 and surrounding zones in accordance with one or more embodiments of the present disclosure. As shown in FIG. 6, the operator side 103-a of the apparatus 100 can include a animal rinse zone 144 and a catheter retraction zone 146 (shown in FIG. 5 as "catheter remove zone" 146). One or more operators can interact with the apparatus 100 during operation. In the animal rinse zone 144, a first operator can cut the pericardial sac of a animal to expose the heart and cut the vena cava of the animal. A second operator can then insert the catheter 116 and start the rinse cycle. After the carriage 105 travels to the catheter retraction zone 146 and rinsing is complete, a third operator can remove the catheter 116. As the catheter 116 continues to travel around to the sanitization side 103-b of the apparatus 100, it can enter a cold wash zone 148 where it can be bathed in water, and then can enter a sanitization zone 150 for sanitization.

The catheter 116 can be washed in the cold wash zone 148 for a minimum period of time, for instance, such as 10 seconds. The cold wash zone 148 can include a bath of ambient temperature water and/or chilled water. In the sanitization zone 150, the catheter 116 can be sprayed with potable filtered water of an elevated temperature (e.g., 85 degrees Celsius) for a minimum period of time (e.g., 15 seconds). In some embodiments, the catheter 116 can be purged using a blast of air. In some embodiments, the catheter 116 can be dried before re-entering the operator side 103-a of the apparatus 100

In some embodiments, the apparatus 100 can be cleaned at a same time as a remainder of a plant in which it operates. For instance, a clean in place (CIP) procedure can be performed by the apparatus 100. In various embodiments, a CIP procedure can include an initial rinse of the apparatus 100, the application of a caustic, a second rinse, and the application of a sanitizer. As previously discussed, a fixed portion 130 of the rotary timing valve 110 can be rotated such that flow of CIP liquids is permitted on the sanitization side 103-b of the apparatus 100 and not on the operator side 103-a.

In some embodiments, brisket sawing may be carried out by the first operator due to chain space availability in a line prior to the animal reaching the apparatus. In some embodiments, duties of operators can be automated. For instance, the removal of the catheter 116 may be automated in some embodiments.

Although specific embodiments have been illustrated and described herein, those of ordinary skill in the art will appreciate that an arrangement calculated to achieve the same results can be substituted for the specific embodiments shown. This disclosure is intended to cover adaptations or variations of various embodiments of the present disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the present disclosure includes other applications in which the above structures and methods are used. Therefore, the scope of various embodiments of the present disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the disclosed embodiments of the present disclosure have to use more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. An apparatus for high speed rinsing solution application, comprising:
   a substructure having an elliptical track;
   a catheter delivery system including a plurality of carriages coupled to the track, wherein each of the carriages includes a respective catheter delivery mechanism;
   a carousel drive system configured to drive the carriages such that the carriages circulate about the substructure on the track;
   a rotary timing valve positioned above a central portion of the substructure, the rotary timing valve including a plurality of outlets each positioned at a respective radial position on the rotary timing valve, wherein each of the plurality of outlets is connected to a respective catheter delivery mechanism by a hose; and
   a hose table positioned between the rotary timing valve and the substructure and configured to support the hoses.

2. The apparatus of claim 1, wherein the apparatus includes and operator side and a sanitizing side.

3. The apparatus of claim 2, wherein a portion of the plurality of outlets of the rotary timing valve on the operator side is configured to output a rinsing solution to a portion of the plurality of catheter delivery mechanisms on the operator side.

4. The apparatus of claim 2, wherein the hose table includes a first elevated lip on the operator side and a second elevated lip on the sanitizing side.

5. The apparatus of claim 4, wherein the hose table is shaped so as to maintain a particular amount of slack in each of the hoses when the carriages are located at any of a plurality of positions on the track.

6. The apparatus of claim 1, wherein the carousel drive system is configured to drive the carriages at a particular speed substantially matching a speed of a conveyor carrying an animal proximal to the apparatus.

7. The apparatus of claim 1, wherein the apparatus includes at least 20 carriages.

8. The apparatus of claim 1, wherein the catheter delivery mechanism includes a shaft portion connected on a first end to a hose portion and connected on a second end to a catheter.

9. The apparatus of claim 8, wherein the apparatus is configured to transfer a rinsing solution from the rotary timing valve through the hose portion, the shaft portion, and the catheter.

10. The apparatus of claim 8, wherein the shaft portion is biased in a first direction by a spring.

11. The apparatus of claim 8, wherein the shaft portion is configured to be pneumatically actuated to move from a first position to a second position.

12. The apparatus of claim 11, wherein the shaft portion is configured to be pulled by an operator from the second position to a third position.

13. A method for high speed rinsing solution application, comprising:
   providing a plurality of carriages coupled to a track, wherein each of the carriages includes a respective catheter delivery mechanism configured to deliver a rinsing solution to a circulatory system of an animal;
   propelling the carriages along the track via a carousel drive system such that the carriages travel along the track in a circuit having a plurality of circumferential positions, wherein the plurality of positions include a first position, a second position, a third position, and a fourth position;
   placing a catheter of the catheter delivery mechanism into a circulatory system of a first animal at the first position;
   delivering the rinsing solution into the circulatory system of the first animal between the first position and the second position;
   removing the catheter from the circulatory system of the first animal at the second position;
   washing the catheter at the third position;
   sanitizing the catheter at the fourth position; and
   placing the catheter into a circulatory system of a second animal at the first position.

14. The method of claim 13, wherein the method includes washing the catheter at the third position with water of an ambient temperature at the third position.

15. The method of claim 13, wherein the method includes sanitizing the catheter with potable filtered water having a temperature of at least 85 degrees Celsius at the fourth position.

16. The method of claim 13, wherein the method includes purging the catheter with air and drying the catheter before placing the catheter into the circulatory system of a second animal at the first position.

17. The method of claim 13, wherein the method includes delivering the rinsing solution into the circulatory system of the first animal while the animal is carried by a moving conveyor between the first position and the second position.

18. An apparatus for high speed rinsing solution application, comprising:
   an operator side and a sanitizing side;
   a substructure having an elliptical track;
   a catheter delivery system including a plurality of carriages coupled to the track, wherein each of the carriages includes a respective catheter delivery mechanism;
   a carousel drive system configured to drive the carriages such that the carriages circulate about the substructure on the track alternately through the operator side and the sanitizing side;

a rotary timing valve positioned above a central portion of the substructure, the rotary timing valve including a plurality of outlets each positioned at a respective radial position on the rotary timing valve, wherein each of the plurality of outlets is connected to a respective catheter delivery mechanism by a hose, wherein a portion of the plurality of outlets of the rotary timing valve on the operator side is configured to output a rinsing solution to a portion of the plurality of catheter delivery mechanisms on the operator side; and a hose table positioned between the rotary timing valve and the substructure and configured to support the hoses, the hose table including a first elevated lip on the operator side and a second elevated lip on the sanitizing side.

19. The apparatus of claim 18, wherein an axis between each major side of the hose table separates the operator side from the sanitizing side.

20. The apparatus of claim 18, wherein the apparatus is positioned such that a portion of a conveyor carrying an animal is below a portion of the plurality of catheter delivery mechanisms on the operator side.

\* \* \* \* \*